US006416792B1

(12) United States Patent
Ingram

(10) Patent No.: US 6,416,792 B1
(45) Date of Patent: Jul. 9, 2002

(54) COMPOSITIONS COMPRISING EQUISETUM AND SYMPHYTUM AND METHODS FOR THE TREATMENT OF SYMPTOMS ASSOCIATED WITH MYCOPLASMA INFECTION

(75) Inventor: Teresa J. Ingram, 1029 State Hwy. 237, Fayetteville, TX (US) 78940

(73) Assignee: Teresa J. Ingram, Fayettesville, TX (US)

( * ) Notice: Subject to any disclaimer, the term of this patent is extended or adjusted under 35 U.S.C. 154(b) by 0 days.

(21) Appl. No.: 09/582,072

(22) PCT Filed: Dec. 4, 1998

(86) PCT No.: PCT/US98/25730

§ 371 (c)(1),
(2), (4) Date: Jun. 21, 2000

(87) PCT Pub. No.: WO99/33480

PCT Pub. Date: Jul. 8, 1999

Related U.S. Application Data

(60) Provisional application No. 60/088,368, filed on Jun. 8, 1998, and provisional application No. 60/068,753, filed on Dec. 24, 1997.

(51) Int. Cl.$^7$ ................................................ A61K 35/78
(52) U.S. Cl. ........................................ 424/725; 424/405
(58) Field of Search ............................. 424/195.1, 725, 424/405

(56) References Cited

U.S. PATENT DOCUMENTS 5,854,291 A  *  12/1998  Laughlin et al. ............ 514/626
5,919,460 A  *  7/1999  Ingram .................... 424/195.1

FOREIGN PATENT DOCUMENTS

| CH | 660451      | * | 4/1987 |
| HU | 44165       | * | 2/1988 |
| RU | 2044547     | * | 9/1995 |
| WO | WO 97/04793 | * | 2/1997 |

* cited by examiner

Primary Examiner—Christopher R. Tate
(74) Attorney, Agent, or Firm—Vinson & Elkins L.L.P.

(57) ABSTRACT

The present invention is directed to compositions containing a combination of a herb from the genus Symphytum together with a herb from the genus Equisetum. These compositions can be extracted and the extract used to alleviate symptoms associated with mycoplasma infection.

19 Claims, No Drawings

US 6,416,792 B1

COMPOSITIONS COMPRISING EQUISETUM AND SYMPHYTUM AND METHODS FOR THE TREATMENT OF SYMPTOMS ASSOCIATED WITH MYCOPLASMA INFECTION

This application claims priority from provisional application Ser. No. 60/088,368, filed Jun. 8, 1998, and provisonal applicaton Ser. No. 60/068,753, filed Dec. 24, 1997.

FIELD OF THE INVENTION

The present invention is directed to compositions and methods that are useful in alleviating the symptoms associated with mycoplasma infection. The compositions and methods involve the use of a combination of any herb in the genus Symphytum together with any herb in the genus Equisetum. In preferred embodiments, compositions and methods utilize *Symphytum officinale* (comfrey) and *Equisetum hyemale* (horsetail).

BACKGROUND OF THE INVENTION

There are a variety of newly characterized diseases that have been associated with infection by polymorphic mycoplasmas which may have a crystalline form, particularly *Mycoplasma fermentans*. Clear links have been established for AIDS and chronic fatigue syndrome (Lo, et al., Clin. Inf. Dis. 3:S259–263 (1993); Lo, et al., Am. J. Trop. Hyg. 41:364–376 (1989)). Other diseases that have been associated with such infections include human bovine spongiform encephalopathy (Rhodes, *Deadly Feasts*, Simon & Schuster, N.Y., N.Y., p. 197 (1997)) and Gulf War syndrome (Nicholson, et al., *Chronic Fatigue Illnesses* and *Operation Desert Storm*, Institute for Molecular Medicine, Irvine, Calif.). Among the many symptoms associated with these diseases are memory loss, dementia, neuropathy, paralysis, loss of motor control and wasting. The mycoplasma infections undoubtedly contribute to these symptoms in at least some patients, and the development of new therapeutic agents for treating such infections is therefore of clear value.

SUMMARY OF THE INVENTION

In its first aspect, the present invention is directed to an herbal mixture that can be used in the preparation of a therapeutic composition for the treatment of subjects suffering from symptoms associated with mycoplasma infection, particularly when such infection occurs in a patient with AIDS, chronic fatigue syndrome, human bovine spongiform encephalopathy, or Gulf War syndrome. The mixture consists essentially of any herb of the genus Symphytum together with any herb of the genus Equisetum. Preferably, the mixture contains *Symphytum officinale* and *Equisetum hyemale*. The herbs used in mixtures may be in any form, but the cut form of the Symphytum herb and the powdered form of the Equisetum herb are generally preferred. Typically, the Symphytum herb should be present at a ratio of about 4.7 parts by weight for each part by weight of Equisetum herb. If desired, an antibiotic may also be added to mixtures.

The mixtures discussed above can be used in a method for preparing a therapeutic composition for administration to a human subject suffering from one or more of the symptoms associated with mycoplasma infection. An aqueous suspension is formed by adding water to the mixture, the suspension is incubated, and undissolved material is then removed to form the final composition. Any herb of the genus Symphylum and any herb of the genus Equisetum may be used in the method but the preferred herbs are *Symphytum officinale* and *Equisetum hyemale*. The Symphytum herb should generally be present at about 4.7 parts by weight for each part by weight of the Equisetum herb. A single unit dose may be obtained by extracting approximately 1.56 g of the herb from the genus Symphytum (e.g., *Symphytum officinale*) and about 0.33 g of the herb from the genus Equisetum (e.g., *Equisetum hyemale*) with 4 to 6 ounces of water at a temperature near its boiling point (e.g., at a temperature of greater than 70 degrees centigrade) for a period of about 10 to 15 minutes. Larger preparations may be prepared as long as the ratio of the various components are kept the same, e.g., there should be about 4 to 6 ounces of water for each 1.5 g of dry Symphytum herb in the mixture. After incubation, any method can be used for clearing preparations of undissolved material but simple filtration will usually be the most convenient. If desired, an antibiotic may be included in the dry mixture of herbs extracted with water or, alternatively, an antibiotic may be added after extraction and filtration.

In addition to being directed to a method for preparing a therapeutic composition, the present invention is also directed to the composition itself and to the use of the composition in treating a human subject for one or more symptoms associated with mycoplasma infection. Typically, subjects will be selected who have AIDS, chronic fatigue syndrome, Gulf War syndrome, or human bovine spongiform encephalopathy and who are also suspected of being infected with mycoplasma. The therapeutic composition should be administered orally in an amount and for a duration sufficient to reduce or eliminate one or more of the subject's symptoms. Preferably, this treatment will also be accompanied by the administration of one or more antibiotics. The mycoplasma symptoms treatable with the composition include enlarged lymph nodes, recurrent headaches, chronic fatigue, persistent weight loss, musculoskeletal pain, recurrent fever, pharyngitis, depression, blurred vision, dizziness, loss of memory and inability to concentrate. Typically, effective treatment will require that the subject take a daily regimen of four to five unit doses of the therapeutic composition for a period of weeks to months and, in some cases, effective therapy may require continued administration for years. The ingestion of the composition for a prolonged period of time will sometimes cause dermatitis. This may be alleviated or avoided by subjects taking dietary supplements of lecithin and maintaining a high daily intake of water.

DETAILED DESCRIPTION OF THE INVENTION

Plants and herbs have long been recognized for their therapeutic properties. Many are known to contain compounds with potent pharmacological actions and medicines have often been developed using plants or herbs as starting material. In the case of the present invention, herbs of the genus Symphytum (e.g., *Symphytum officinale* or *Symphytum uplandicum*) are known to contain allantoin, alkaloids and lithospermic acid. Herbs of the genus Equisetum, (e.g., *Equisetum hyemale*) are known to contain silica. It has been found that a mixture of these herbs may be extracted with water and the extract used to help alleviate certain of the symptoms associated with mycoplasma infection, particularly when the extract is used in conjunction with an antibiotic.

A single unit dose of the composition may be made by combining about 1.56 g of Symphytum herb, preferably in its cut form, with approximately 0.33 g of Equisetum herb, preferably in its powdered form. The dry herbs are placed in an appropriate container and water, heated to a temperature near its boiling point (e.g., to a temperature of greater than 70 degrees centigrade), is then added to a final volume of about 240 ml. The resulting suspension should be covered and incubated for a period of between 10 and 15 minutes. At the end of the incubation, the undissolved herbal material may be removed by straining and the recovered fluid can then be taken orally by patients. This therapeutic composition may be prepared immediately before administration, or, alternatively, one or more preparations may be stored either frozen or lyophilized until use.

One particularly desirable means for preparing the present therapeutic composition is to store premeasured unit dose amounts of dry herbs in porous disposable containers similar to those presently used in teas. Alternatively, dried extract can be incorporated into traditional oral dosage forms such as tablets or capsules. Typically, these would also contain one or more pharmaceutically acceptable excipients.

Patients suffering from symptoms associated with mycoplasma infection should take between four and five unit doses of the composition described above, roughly 960 to 1200 ml, daily. Preferably, this dosage should be spread out relatively evenly throughout the day. Individuals taking other medications may find it desirable to begin with a lower dosage and gradually increase the amount taken over a period of time. This should minimize the chance of their experiencing any severe side effects due to interaction between agents within the therapeutic composition and the other drugs being taken. It is highly preferred that administration of an antibiotic occur concurrently with the administration of the therapeutic composition for part, or preferably all, of the therapy. The duration of treatment necessary to reduce or eliminate symptoms will vary from weeks to years.

The main side effect associated with the administration of the pharmaceutical composition is dermatitis. This may be partially alleviated or avoided by supplementing a patient's diet with lecithin and by ensuring that the patient drinks adequate daily amounts of water. If desired, other dietary supplements may also be used without altering the effectiveness of therapeutic compositions.

All references cited are fully incorporated by reference. Having now fully described the invention, it will be understood by those of skill in the art that the invention may be performed within a wide and equivalent range of conditions, parameters, and the like, without effecting the spirit or scope of the invention or any embodiment thereof.

What is claimed is:

1. An herbal mixture useful in the preparation of a pharmaceutical composition for treating mycoplasma symptoms in a human subject, wherein said composition is orally administered and comprises an effective amount of said mixture, and wherein said mixture consists essentially of:
   a) an effective amount of an aqueous extract of *Symphytum officinale*; and
   b) an effective amount of an aqueous extract of *Equisetum hyemale*.

2. The mixture of claim 1, wherein said *Symphytum officinale* is present at about 4.7 parts by weight for each part by weight of *Equisetum hyemale*.

3. The method of claim 1, wherein said aqueous extract of *Symphytum officinale* or said aqueous extract of *Equisetum hyemale* comprises dried material.

4. A method of preparing a therapeutic composition for oral administration to a human subject suffering from one or more symptoms associated with mycoplasma infection, said method comprising:
   a) preparing a mixture consisting essentially of:
      i) an effective amount of an aqueous extract of *Symphytum officinale*; and
      ii) an effective amount of an aqueous extract of *Equisetum hyemale*;
   b) adding water to the mixture of step a) to form an aqueous suspension;
   c) incubating the aqueous suspension of step b); and
   d) removing the undissolved material from the incubate of stem c).

5. The method of claim 4, wherein said herb of the genus Symphytum is present at about 4.7 parts by weight for each part by weight of herb of the genus Equisetum.

6. The method of claim 4, wherein about 4–6 ounces of said water are added for each 1.5 g of herb of the genus Symphytum in said mixture.

7. The method of claim 4, wherein said water added to the mixture of step a) is at a temperature at or near its boiling point.

8. The method of claim 4, wherein said undissolved material is removed from said aqueous suspension by filtration.

9. The method of claim 4, further comprising the addition of antibiotic to said therapeutic composition.

10. The therapeutic composition produced by the method of claim 4.

11. A method of treating a human subject exhibiting one or more symptoms associated with mycoplasma infection, said method comprising administering the therapeutic composition of claim 10 to said human subject in an amount and for a duration sufficient to reduce or eliminate said symptoms.

12. The method of claim 11, further comprising administering an antibiotic to said human subject.

13. The method of claim 11, wherein said symptoms are selected from the group consisting of: enlarged lymph nodes; recurrent headaches; chronic fatigue; persistent weight loss; musculoskeletal pain; recurrent fever; pharyngitis; depression; blurred vision; dizziness; loss of memory; and inability to concentrate.

14. The method of claim 13, further comprising the administration of antibiotic to said human subject.

15. The method of claim 11, further comprising the administration of a lecithin dietary supplement to said human subject.

16. The method of claim 4 wherein said aqueous extract of *Symphytum officinale* or said aqueous extract of *Equisetum hyemale* comprises dried material.

17. An herbal useful in the preparation of a pharmaceutical composition for treating mycoplasma symptoms, said mixture consisting essentially of:
   a) an aqueous extract of *Symphytum officinale*; and
   b) an aqueous extract of *Equisetum hyemale*;
   c) an antibiotic.

18. The mixture of claim 17, wherein the *Symphytum officinale* is present at about 4.7 parts by weight for each part by weight of *Equisetum hyemale*.

19. The method of claim 17 wherein said aqueous extract of *Symphytum officinale* or said aqueous extract of *Equisetum hyemale* comprises dried material.

* * * * *